United States Patent [19]

Barnes, Jr. et al.

[11] 4,080,653
[45] Mar. 21, 1978

[54] INTRACRANIAL PRESSURE DATA PROCESSOR

[76] Inventors: Ralph W. Barnes, Jr., 440 Flynt Valley Dr., Winston-Salem, N.C. 27104; C. Patrick McGraw, 6924 Harper Valley, Clemmons, N.C. 27012

[21] Appl. No.: 654,045

[22] Filed: Jan. 30, 1976

[51] Int. Cl.² .................. G01V 1/28; A61B 9/00
[52] U.S. Cl. ................. 364/417; 128/2 R; 235/92 DP
[58] Field of Search .......... 235/151.3, 92 MT, 92 PC, 235/92 PB, 92 DP; 128/2 R, 2 N, 2.05 E, 2.05 R; 324/71 CP

[56] References Cited

U.S. PATENT DOCUMENTS

| | | | |
|---|---|---|---|
| 3,219,803 | 11/1965 | Jones | 235/92 MT |
| 3,836,849 | 9/1974 | Coulter et al. | 324/71 CP |
| 3,851,156 | 11/1974 | Green | 235/151.3 |
| 3,955,070 | 5/1976 | Suzuki et al. | 235/92 MT |
| 3,985,123 | 10/1976 | Herzlinger et al. | 235/151.3 |

Primary Examiner—Felix D. Gruber
Assistant Examiner—Errol A. Krass

[57] ABSTRACT

The present invention relates to a method of and apparatus for processing physiological information and particularly to a method and device for the processing of intracranial pressure data, such as the information which is sensed by a transducer amplifier responsive to a patient's intracranial pressure. The invention is especially suitable for use in processing intracranial pressure readings over a period of time to obtain data which may be useful in prognosis.

12 Claims, 4 Drawing Figures

INTRACRANIAL PRESSURE DATA PROCESSOR

BACKGROUND, BRIEF SUMMARY, AND OBJECTIVES OF THE INVENTION

The analysis of intracranial pressure records is laborious and time-consuming when done manually because this type record is normally a continuous chart reflecting meaningful fluctuations in intracranial pressure over an extended period of time. To review such a chart in detail requires a considerable amount of the doctor's time and study. Moreover, periodic reviews or spot checks of such a chart may not accurately reflect the true state of the patient's condition since the chart may not be observed over the entire recording period even though the record is continuous.

It is obvious that intracranial pressure continuous charts must be thoroughly analyzed to detect pressure variations that may be significant for therapy and prognosis if the record is to have any value at all. Previous research has resulted in the use of a computer situated at a remote location to classify intracranial pressure readings into discrete pressure ranges and to construct a histogram of percentage time the intracranial pressure was within each pressure range.

A significant improvement in the analysis of intracranial pressure data has now been achieved by processing the data with a computer on-line at the patient's bedside. The on-line intracranial pressure data processor performs the necessary classification and calculations to display an amplitude analysis of the data in the familiar histogram form.

Intracranial pressure data from the transducer amplifier receiving intracranial pressure readings directly from the patient is appropriately amplified and introduced to an analog-to-digital convertor and then transmitted to a classifier which determines the pressure range of the current sample. A predetermined number, sixteen for example, of pressure ranges are provided. If the intracranial pressure sample value falls within a given pressure range, a count pulse is entered in the corresponding pressure range counter. A count pulse is also entered into the number of sample pulses processed counter. The instrument then sequentially calculates the number of pulses in each pressure range counter divided by the total number of samples processed. This percentage time calculation is performed to an accuracy of two decimal places. Each result is stored in the percentage memory. A histogram of the percentage time is presented on the front panel of the instrument. Pressure range is selectible by a display selector switch on that panel.

Additional data controlled by the display selector switch and displayed on the numerical display are: (1) the value of the last intracranial pressure data sample, and (2) the time in hours and minutes of the observation of the intracranial pressure data processed on-line.

From the foregoing discussion, it can be seen that it is a principal object of the present invention to provide an improved method and apparatus for processing of physiological information, such as intracranial pressure data, which automatically provides a visual display of meaningful information useful in diagnosis and other clinical purposes.

It is another object of this invention to provide improved apparatus and method for analysis of physiological information such as intracranial pressure acquired over a long period of time, which method and apparatus is operative to reduce the information into a form which permits analysis of the patient's condition that is of immediate interest at the patient's bedside.

It is still another object of the invention to provide an improved method and apparatus for immediate and instantaneous accumulation of intracranial pressure data in a manner not previously attainable.

It is yet a further object of the present invention to provide additional visual data such as the value of the last intracranial pressure data sample and the time in hours and minutes of the observation of the intracranial pressure data processed on-line.

The invention itself as well as the foregoing objectives and other objects, features, and advantages thereof, will be more clearly understood from the following detailed description taken in conjunction with the accompanying drawings wherein like characters of reference designate like parts throughout the several views.

FIGURE DESCRIPTION

DETAILED DESCRIPTION OF THE DISCLOSURE

Figure 3:
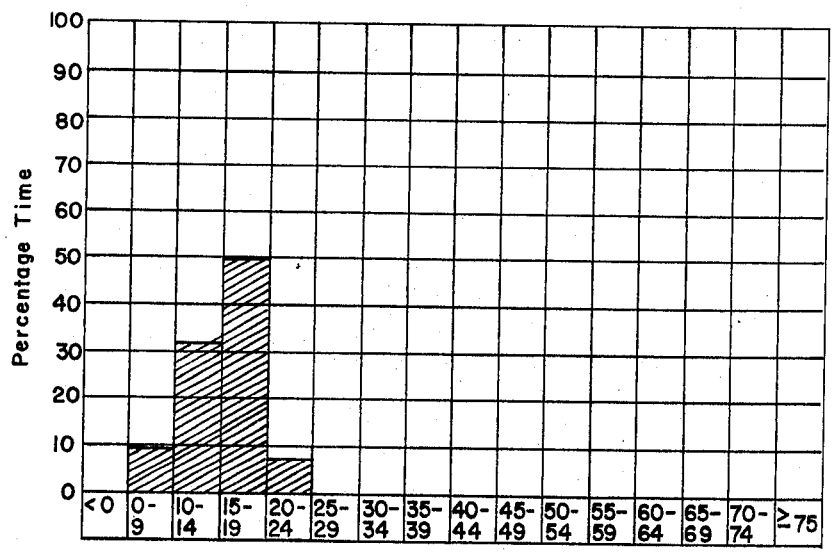
FIG. 3 is a histogram conventionally used to accumulate intracranial pressure data in a meaningful manner.

It is necessary that intracranial pressure continuous recording charts be thoroughly analyzed by the physician if meaningful pressure variations that may be significant in therapy and prognosis are to be noted and if the record is to have any overall significance. Previous efforts have resulted in the use of a computer to classify intracranial pressure readings into discrete pressure ranges and to construct a histogram of percentage time that the intracranial pressure was within each pressure range. An illustrative histogram is shown in FIG. 3. In most cases, however, meaningful data must be manually extracted from the continuous recording charts and grouped by a computer to form a useful histogram; and this can only be accomplished after passage of a significant period of time. After the passage of even 1 hour's time, the data may be of limited value.

The present invention is a development that permits the analysis of intracranial pressure data with a computer on-line at the patient's bedside. The on-line intracranial pressure data processor performs the necessary classification and calculations to display immediately an amplitude analysis of the data in the familiar histogram.

Figure 1:
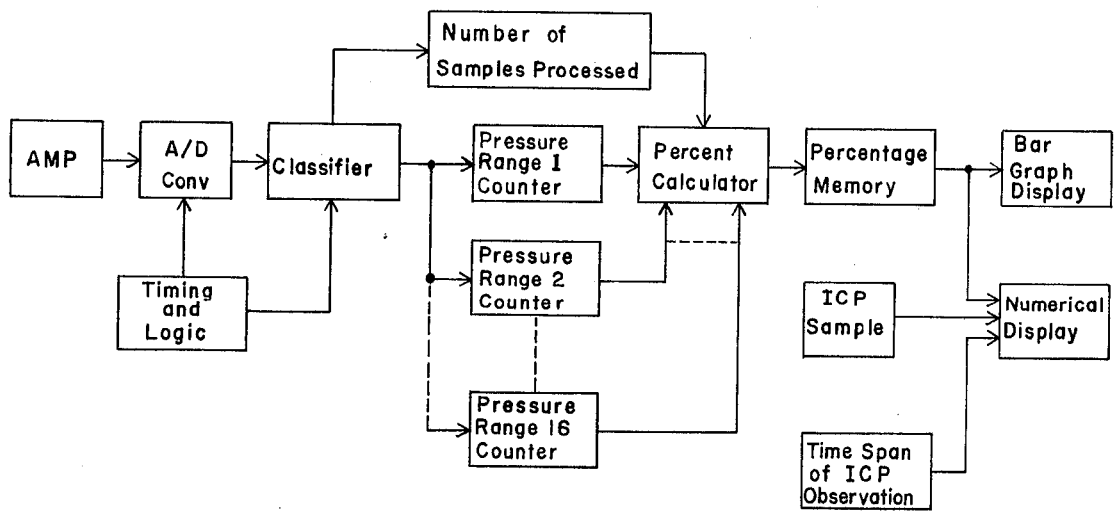
FIG. 1 is a simplified block diagram of the on-line data processor for the instantaneous evaluation of intracranial pressure at the patient's bedside.
Figure 2:
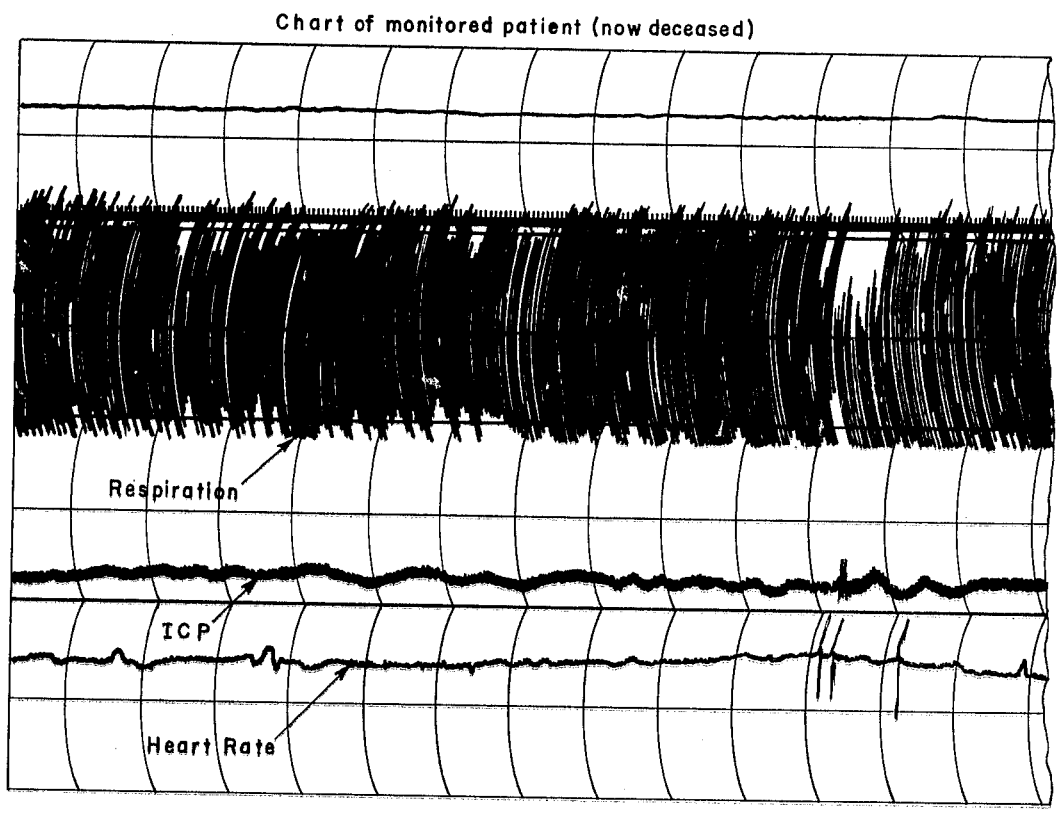
FIG. 2 is a conventional continuous recording chart showing intracranial pressure.

A block diagram of the on-line data processor is shown in FIG. 1. Intracranial pressure data from the transducer amplifier 10 receiving intracranial pressure readings directly from the patient is appropriately amplified and fed to an analog-to-digital convertor 12. The output of the analog-to-digital convertor 12 is transmitted to a classifier 14 which senses the pressure range of the current sample. A predetermined number, for example sixteen, of pressure ranges are provided with a pressure range counter 16 designated for each range. If the intracranial pressure sample value falls within a given pressure range, a count pulse is entered in the corresponding pressure range counter 16. Each such counter has a maximum of 9,999 counts. A count pulse is also entered into the total number of samples processed counter 18.

Figure 4:
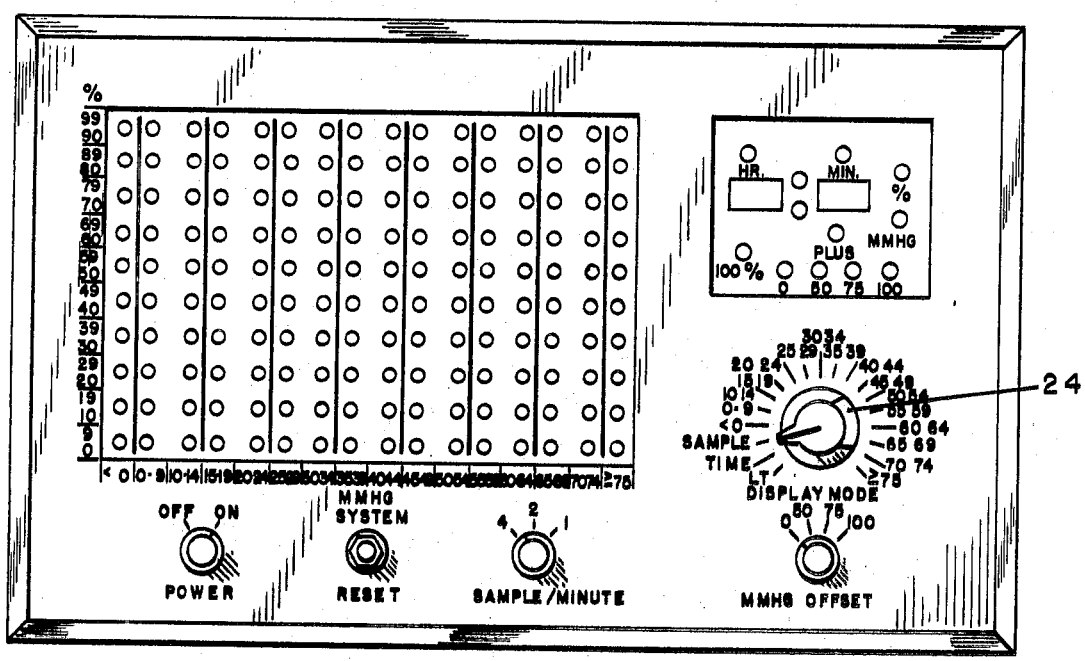
FIG. 4 is a display panel of the on-line data processor embodying the present invention.

A percent calculator 20 then sequentially calculates the number of pulses in each pressure range counter divided by the total number of samples processed. This percentage time calculation is performed to an accuracy of two decimal places. Each result is stored in a percentage memory 22. A histogram such as shown in FIG. 3 of the percentage time to one decimal place is presented on the display panel of the instrument (FIG. 4). However, the percentage time calculation is available to two decimal places on the numerical display. Pressure range is selectible by a display selector switch 24 on the front panel as can be seen in FIG. 4.

Additional data controlled by the display selector switch and displayed on the numerical display are (1) the value of the last intracranial pressure data sample, and (2) the total period of time of the observation of the intracranial pressure data processed on-line.

The timing and logic block controls the internal operation and the intracranial pressure sampling rate. Intracranial pressure data can be sampled at 15, 30, or 60-second intervals, and the total number of sample ranges from 1,440 to 5,760 samples per 24-hour period.

Sequential histograms provided by the on-line intracranial pressure data processors should provide information for day-to-day or even hour-to-hour comparisons of the intracranial pressure distribution throughout the 16 ranges. Moreover, the on-line processed information is extremely valuable in analyzing intracranial pressure in relation to patient progress and therapeutic efficacy.

Use of the present development is readily appreciated since instantaneously collected intracranial pressure data is immediately grouped into pressure classes and the pressure class frequency distribution is conveniently represented as a histogram by plotting the number of observations (expressed as percentages of the total) against the pressure classes. The doctor is able to instantaneously review the patient's history over an extended period of time by desired control activation and thus avoid the tedious examination and analysis normally associated with continuous recording charts. The information is thus immediately available. Pressure ranges for intracranial pressure and time percentages are visibly reviewable. From this display an indication of the magnitude and time duration of transient intracranial pressure and its relevance to patient therapy and prognosis can be obtained. Even when continuous charts have been studied and consolidated into histograms like those illustrated and described herein, the data is, by necessity, old and may not be useful for immediate therapy and prognosis.

While the present invention is related primarily to the processing of intracranial pressure data, it is to be understood that the on-line accumulation and grouping of data such as blood pressure, perfusion pressure, and cerebral blood flow for therapy and prognosis can be readily applied in other areas where physiological information must be studied and analyzed over a period of time. It will also be appreciated that other variations and modifications in the hereindescribed system will undoubtedly become apparent to those skilled in the art.

It is intended that the foregoing description be considered merely as illustrative and not limiting in any sense.

We claim:

1. Apparatus for instantaneously processing data relating to intracranial pressure to display an immediate amplitude analysis of the data comprising: means responsive to intracranial pressure; classifying means sensing a predetermined number of pressure ranges; a plurality of pressure range counters, said classifying means entering a sensed count pulse in the corresponding pressure range counter as the pulse is received; percent calculator means calculating the number of counts in each pressure range counter divided by the total number of pressure count samples processed; percentage memory means storing each calculated result from said percent calculator means; display means illustrating bar graph and numerical data; and display selector means selectively actuating said display means illustrating bar graph and numerical data.

2. The apparatus as claimed in claim 1 wherein said classifying means enters a sensed pulse count commensurate with intracranial pressure every 15 seconds.

3. The apparatus as claimed in claim 1 wherein said classifying means enters a sensed pulse count commensurate with intracranial pressure every 30 seconds.

4. The apparatus as claimed in claim 1 wherein said classifying means enters a sensed pulse count commensurate with intracranial pressure every 60 seconds 5. The apparatus as claimed in claim 1 wherein the bar graph data is displayed as a histogram formed by plotting the number of sensed count pulses expressed as percentages of the total count samples against the individual pressure ranges.

6. The apparatus as claimed in claim 5 wherein the numerical data displayed is the value of the most recent intracranial pressure sample.

7. The apparatus as claimed in claim 6 wherein the numerical data displayed is the time in hours and minutes of processed intracranial pressure data.

8. The apparatus as claimed in claim 1 wherein the numerical data displayed is the value of the most recent intracranial pressure sample.

9. The apparatus as claimed in claim 1 wherein the numerical data displayed is the time in hours and minutes of processed intracranial pressure data.

10. The apparatus as claimed in claim 1 wherein said pressure range counters number 16.

11. The method of instantaneously processing data relating to intracranial pressure to provide an immediate amplitude analysis of the processed data comprising the steps of: receiving intracranial pressure pulses from a responsive transducer; instantaneously grouping the pulses into a predetermined number of pressure ranges; calculating the number of counts in each range divided by the total number of pressure pulses processed; and displaying immediately data, said data being a histogram formed by plotting the number of count samples expressed as percentages of the total pulses against the individual pressure ranges.

12. The method as claimed in claim 11 wherein said data is also numerical data showing the most recent intracranial pressure sample and the total time period of the observed and processed data recordings.

* * * * *